United States Patent [19]
Ito et al.

[11] Patent Number: 5,663,458
[45] Date of Patent: Sep. 2, 1997

[54] PROCESS FOR PRODUCING α-PHENYLETHYL ALCOHOL

[75] Inventors: Shinya Ito, Sodegaura; Takuo Hibi, Ichihara, both of Japan

[73] Assignee: Sumitomo Chemical Company, Limited., Osaka, Japan

[21] Appl. No.: 564,637

[22] Filed: Nov. 29, 1995

[30]  Foreign Application Priority Data

| Dec. 2, 1994 | [JP] | Japan | 6-299395 |
| Feb. 16, 1995 | [JP] | Japan | 7-028297 |
| Sep. 14, 1995 | [JP] | Japan | 7-236878 |

[51] Int. Cl.$^6$ ............................................. C07C 29/14
[52] U.S. Cl. ........................ 568/814; 568/799; 568/715
[58] Field of Search ............................. 568/799, 814, 568/715

[56]  References Cited

U.S. PATENT DOCUMENTS

| 2,125,412 | 8/1938 | Arnold et al. | 260/154 |
| 2,137,407 | 11/1938 | Lazier | 260/638 |
| 2,334,100 | 11/1943 | Ipatieff et al. | 260/668 |
| 2,400,959 | 5/1946 | Stewart . | |
| 2,544,756 | 3/1951 | Guest et al. | 252/470 |
| 2,554,771 | 5/1951 | Bach | 20/67 |
| 2,575,403 | 11/1951 | Young et al. | 260/618 |
| 2,575,404 | 11/1951 | Guest et al. | 260/618 |
| 3,927,120 | 12/1975 | Grane et al. | 260/618 |
| 3,927,121 | 12/1975 | Grane et al. | 260/618 |
| 4,160,746 | 7/1979 | Rashkin | 252/468 |
| 4,208,539 | 6/1980 | Rashkin . | |
| 5,243,095 | 9/1993 | Roberts et al. . | |
| 5,345,005 | 9/1994 | Thakur et al. . | |

FOREIGN PATENT DOCUMENTS

| 0604792A1 | 7/1994 | European Pat. Off. . |
| 59-27216 | 7/1984 | Japan . |
| 1-25730 | 5/1989 | Japan . |
| 1507555 | 4/1978 | United Kingdom . |

OTHER PUBLICATIONS

CA File Search Results –P005079C Jan. 5, 1994.
Kazuhiko Saeki et al, "Preparation of Aromatic Carbinols", p. 654, *Chemical Abstracts*, vol. 113, No. 7, 13 Aug. 1990, Abstract No. 58673q.

*Primary Examiner*—Alan L. Rotman
*Assistant Examiner*—Sreeni Padmanabhan
*Attorney, Agent, or Firm*—Sughrue, Mion, Zinn, Macpeak & Seas

[57]  ABSTRACT

According to a process for producing α-phenylethyl alcohol by hydrogenation of acetophenone, which uses a copper-based catalyst containing at least one alkaline earth metal carbonate and/or at least one alkali metal compound, the hydrogenolysis of starting acetophenone is inhibited, and hence the production of ethylbenzene as a by-product is reduced, so that it becomes possible to produce α-phenylethyl alcohol useful as a starting material for styrene with high selectivity.

21 Claims, No Drawings

PROCESS FOR PRODUCING α-PHENYLETHYL ALCOHOL

FIELD OF THE INVENTION

The present invention relates to a process for producing α-phenylethyl alcohol.

More particularly, the present invention relates to a process for producing α-phenylethyl alcohol by hydrogenation of acetophenone, which uses a safer and more active catalyst not containing a large amount of chromium oxide, hardly causes hydrogenolysis of starting acetophenone, gives only a slight amount of ethylbenzene as a by-product, and hence has a high selectivity for the desired compound α-phenylethyl alcohol.

BACKGROUND OF THE INVENTION

α-Phenylethyl alcohol is useful as a starting material for styrene and is well known to be obtainable by hydrogenation of acetophenone. For example, JP-B-59-27216 discloses a process in which acetophenone is hydrogenated using a copper-chromite catalyst containing barium, magnesium and zinc.

Conventional processes using a copper-chromite catalyst, however, involve the following problems: the hydrogenation catalyst is poor in safety and hygienic properties in handling because of its high chromium oxide content and has a low activity, and the amount of ethylbenzene produced as a by-product is large, resulting in a low selectivity for α-phenylethyl alcohol.

In view of such conditions, the present inventors earnestly investigated a process for producing α-phenylethyl alcohol which is free from the above problems, and consequently found that α-phenylethyl alcohol can be produced with high selectivity by inhibiting the production of ethylbenzene as a by-product by the use of a copper-based catalyst containing an alkali metal compound and/or an alkaline earth metal carbonate which hardly involves safety and hygienic problems.

SUMMARY OF THE INVENTION

The present invention provides a process for producing α-phenylethyl alcohol by hydrogenation of acetophenone, which uses a copper-based catalyst containing at least one alkaline earth metal carbonate and/or at least one alkali metal compound.

DETAILED DESCRIPTION OF THE INVENTION

The catalyst used in the present invention is a copper-based catalyst containing at least one alkaline earth metal carbonate and/or at least one alkali metal compound.

The alkali metal compound includes carbonates, nitrates, hydroxides, hydrogencarbonates, etc. of alkali metals. The alkali metals include lithium, sodium, potassium, rubidium, cecium, etc. Specifically, there is preferably used carbonate, nitrate or hydrogen-carbonate of sodium or potassium, more preferably carbonate of sodium, potassium or sodium nitrate.

In the present invention, the above-exemplified alkali metal compounds may be used singly or in combination of two or more thereof.

The alkaline earth metal carbonate includes, for example, carbonates of magnesium, calcium, strontium, barium, etc. Preferable examples thereof are carbonates of strontium, calcium and barium. A more preferable example thereof is strontium carbonate.

In the present invention, the above-exemplified alkaline earth metal carbonates may be used singly or in combination of two or more thereof.

The copper-based catalyst used in the present invention is composed mainly of copper and may contain, besides copper, manganese, aluminum, cobalt, zinc, ruthenium, iron and zirconium compounds in an amount of 10 wt % or less based on the weight of copper.

When the catalyst used in the present invention contains the alkali metal compound(s), the content of the compound (s) ranges preferably from 0.01 to 10 wt %, more preferably 0.01 to 5 wt %, (in terms of the alkali metal(s)) based on the weight of the catalyst before its reduction. The incorporation of the alkali metal compound(s) into the catalyst in the above range permits enhancement of the activity of the catalyst and inhibition of hydrogenolysis.

When the catalyst used in the present invention contains the alkaline earth metal carbonate(s), the weight ratio of the alkaline earth metal carbonate(s) to metallic copper ranges preferably from 0.1:99.9 to 50:50, more preferably from 0.1:99.9 to 25:75. When the amount of the alkaline earth metal carbonate(s) is too small, the catalyst has a low activity and the inhibitory effect on hydrogenolysis is small in some cases. When the amount is too large, the hydrogenating activity of the catalyst is low in some cases.

The catalyst according to the present invention may be used either after being supported on a carrier or without a carrier.

When the catalyst is supported on a carrier, the weight ratio of metallic copper to the carrier ranges usually 20:80 to 90:10.

When the catalyst is supported on a carrier, the carrier includes metal oxides (e.g. silica, alumina, titania and diatomaceous earth) and metal mixed oxides. In particular, silica and diatomaceous earth are preferable.

The catalyst according to the present invention can be produced, for example, by a coprecipitation method, a precipitation method, a mixing method, or the like, and is preferably produced by the coprecipitation method.

There is explained below a process for producing, as a typical example of the catalyst, a copper-based catalyst supported on silica which contains an alkaline earth metal carbonate and an alkali metal compound.

When the catalyst is produced by the coprecipitation method, an alkali solution such as an alkali metal carbonate solution, ammonium carbonate solution or the like is added to a mixed solution of a copper salt and a salt of the alkaline earth metal to cause coprecipitation, and the resulting precipitate is filtered, washed, and then mixed with a silica carrier, followed by drying and calcination.

Subsequently, the calcined catalyst is mixed with an aqueous solution of the alkali metal compound and the resulting mixture is dried and reduced by hydrogen, whereby there can be produced the copper-based catalyst supported on silica which contains the alkali metal compound and the alkaline earth metal carbonate.

In this case, when a solution of the alkali metal compound is used as the alkali solution, the copper-based catalyst supported on silica can be produced also by leaving the alkali metal compound by controlling, for example, the washing after the filtration, and drying the resulting residue, followed by calcination and reduction with hydrogen.

The aforesaid copper salt includes, for example, nitrate, sulfate, halide, organic acid salts, etc. The salt of the alkaline earth metal includes nitrate, chloride, etc. of the alkaline earth metal. The alkali includes, for example, carbonates, hydroxides and hydrogencarbonates of alkali metals, aqueous ammonia, and ammonium carbonate. The alkali metal compound includes, for example, carbonates, nitrates, hydroxides, hydrogen-carbonates and organic acid salts of alkali metals. These alkali metals include lithium, sodium, potassium, rubidium, cesium, etc. The above-exemplified alkalis and alkali metal compounds are usually used in the form of an aqueous solution, a solution in an organic solvent such as metanol, or a mixture thereof. The precipitation temperature ranges usually from room temperature to about 100° C. The calcination is carried out in air at 300° to 500° C. for usually about 30 minutes to about 10 hours. The reduction by hydrogen is carried out at 100° to 500° C. for usually about 30 minutes to about 20 hours.

When the catalyst is produced by the precipitation method, the alkaline earth metal carbonate and a silica carrier are suspended in a copper salt solution, and then an alkali solution is added thereto to precipitate copper and support the same on the alkaline earth metal carbonate and the silica carrier, followed by filtration, washing, drying and calcination.

Subsequently, the calcined catalyst is mixed with an aqueous solution of the alkali metal compound and the resulting mixture is dried and reduced by hydrogen, whereby there can be produced the copper-based catalyst supported on silica which contains the alkali metal compound and the alkaline earth metal carbonate.

In this case, when a solution of the alkali metal compound is used as the alkali solution, the copper-based catalyst supported on silica can be produced also by leaving the alkali metal compound by controlling, for example, the washing after the filtration, and drying the resulting residue, followed by calcination and reduction with hydrogen. As the copper salt, the same salts and complex compounds as above can be exemplified. As the alkali and the alkali metal compound, the same alkalis and alkali metal compounds as above can be exemplified. The precipitation conditions, the calcination conditions and the conditions of the reduction with hydrogen are usually the same as in the coprecipitation method.

When the catalyst is produced by the mixing method, an alkali solution is added to a copper salt solution to form a precipitate, and then the alkaline earth metal carbonate and a silica carrier are mixed with the precipitate, followed by filtration, washing, drying and calcination.

Subsequently, the calcined catalyst is mixed with an aqueous solution of the alkali metal compound and the resulting mixture is dried and reduced by hydrogen, whereby there can be produced the copper-based catalyst supported on silica which contains the alkali metal compound and the alkaline earth metal carbonate.

In this case, when a solution of the alkali metal compound is used as the alkali solution, the copper-based catalyst supported on silica can be produced also by leaving the alkali metal compound by controlling, for example, the washing after the filtration, and drying the resulting residue, followed by calcination and reduction with hydrogen. As the copper salt, the same salts and complex compounds as above can be exemplified. As the alkali and the alkali metal compound, the same alkalis and alkali metal compounds as above can be exemplified. The precipitation conditions, the calcination conditions and the conditions of the reduction with hydrogen are usually the same as in the coprecipitation method.

The catalyst used in the present invention may contain a lubricant such as graphite to be used at the time of molding of the catalyst.

The catalyst may also contain a binder. The binder includes organic binders and inorganic binders such as silica sol.

The present invention provides a process for producing α-phenylethyl alcohol by hydrogenation of acetophenone by the use of the specific copper-based catalyst described above.

The hydrogenation reaction can be carried out either by a batch method or by a flow method. When the flow method is adopted, a fixed-bed liquid phase flow method is usually adopted and either an up-flow method or a down-flow method may be adopted.

The reaction temperature ranges preferably from 0° to 200° C., more preferably from 50° to 200° C. The reaction pressure ranges preferably approximately from 5 to 100 atmospheres.

When the batch method is adopted, the weight ratio of the catalyst used to a compound to be reduced ranges preferably approximately from 0.001:1 to 0.5:1, and the reaction time ranges preferably approximately from 30 minutes to 10 hours. When the flow method is adopted, the feed rate (LHSV) of a solution of a compound to be reduced ranges preferably approximately from 0.05 to 10 $h^{-1}$, more preferably approximately from 0.1 to 5 $h^{-1}$.

When the batch method is adopted, the amount of hydrogen used for the hydrogenation reaction is regulated by the reaction pressure and a hydrogen pressure of 100 atmospheres or less is preferable. When the flow method is adopted, it is preferable to supply hydrogen in an amount of approximately 1 to 30 times larger than the theoretical molar equivalent of hydrogen to the compound to be reduced.

According to the present invention, the hydrogenolysis of starting acetophenone is inhibited, and hence the production of ethylbenzene as a by-product is reduced, so that it becomes possible to produce α-phenylethyl alcohol useful as a starting material for styrene with high selectivity.

The present invention is more concretely explained with reference to the following examples, which should not be construed as limiting the scope of the invention.

EXAMPLES

Catalyst Preparation Example 1

48.32 g of copper nitrate trihydrate and 0.91 g of strontium nitrate were dissolved in 400 ml of water, and the resulting solution was heated to 50° C. Then, a solution of 36.81 g of sodium carbonate in 200 ml of water was added dropwise with stirring over a period of 1 hour, after which the stirring was continued at the same temperature for 2 hours. The precipitate thus formed was collected by filtration and then washed 8 times with 1,000 ml of warm water of 50° C. Subsequently, a suspension of 16.80 g of Aerosil Silica in 1,000 ml of warm water of 50° C. was added to the washed precipitate, and the resulting mixture was stirred for 20 minutes and then filtered. The residue was dried at 60° C. and pulverized to obtain 36.69 g of a brown powder. This powder was heated in air at 350° C. for 5 hours and then cooled to room temperature to obtain 34.56 g of a black powder. Subsequently, this solid was heated in a hydrogen stream at 180° C. for 5 hours to obtain copper-based catalyst A. As a result of analysis, the weight ratio of metallic copper to strontium carbonate in the catalyst was found to be 99.1:0.9, and the alkali metal content of the catalyst was found to be 0.03 wt % based on the catalyst's weight before the reduction with hydrogen.

Catalyst Preparation Example 2

Copper-based catalyst B was prepared according to the Catalyst Preparation Example 1 except for adding a solution of 0.0250 g of sodium carbonate in 40 ml of water to 5.0 g of the black powder obtained by the heating in air, and then evaporating the water with a rotary evaporator to support sodium carbonate on the solid by impregnation. As a result of analysis, the weight ratio of metallic copper to strontium carbonate in the catalyst was found to be 99.1:0.9, and the alkali metal content of the catalyst was found to be 0.24 wt% based on the catalyst's weight before the reduction with hydrogen.

Catalyst Preparation Example 3

Copper-based catalyst C was prepared according to the Catalyst Preparation Example 1 except for changing the amounts of copper nitrate trihydrate, strontium nitrate and sodium carbonate used to 43.49 g, 1.82 g and 34.00 g, respectively. As a result of analysis, the weight ratio of metallic copper to strontium carbonate in the catalyst was found to be 94.4:5.6, and the alkali metal content of the catalyst was found to be 0.02 wt% based on the catalyst's weight before the reduction with hydrogen.

Catalyst Preparation Example 4

Copper-based catalyst D was prepared according to the Catalyst Preparation Example 3 except for adding a solution of 0.0253 g of sodium carbonate in 40 ml of water to 5.0 g of the black powder obtained by the heating in air, and then evaporating the water with a rotary evaporator to support sodium carbonate on the solid by impregnation. As a result of analysis, the weight ratio of metallic copper to strontium carbonate in the catalyst was found to be 94.0:6.0, and the alkali metal content of the catalyst was found to be 0.24 wt% based on the catalyst's weight before the reduction with hydrogen.

Catalyst Preparation Example 5

Copper-based catalyst E was prepared according to the Catalyst Preparation Example 1 except for changing the amounts of copper nitrate trihydrate, strontium nitrate and sodium carbonate used to 38.66 g, 3.64 g and 31.90 g, respectively. As a result of analysis, the weight ratio of metallic copper to strontium carbonate in the catalyst was found to be 86.8:13.2, and the alkali metal content of the catalyst was found to be 0.02 wt% based on the catalyst's weight before the reduction with hydrogen.

Catalyst Preparation Example 6

Copper-based catalyst F was prepared according to the Catalyst Preparation Example 5 except for adding a solution of 0.0245 g of sodium carbonate in 40 ml of water to 5.0 g of the black powder obtained by the heating in air, and then evaporating the water with a rotary evaporator to support sodium carbonate on the solid by impregnation. As a result of analysis, the weight ratio of metallic copper to strontium carbonate in the catalyst was found to be 86.8:13.2, and the alkali metal content of the catalyst was found to be 0.23 wt% based on the catalyst's weight before the reduction with hydrogen.

Catalyst Preparation Example 7

48.32 g of copper nitrate trihydrate was dissolved in 400 ml of water and the resulting solution was heated to 50° C. Then, a solution of 36.04 g of sodium carbonate in 200 ml of water was added dropwise with stirring over a period of 1 hour, after which the stirring was continued at the same temperature for 2 hours. The precipitate thus formed was collected by filtration and then washed 8 times with 1,000 ml of warm water of 50° C. Subsequently, a suspension of 16.00 g of Aerosil Silica in 1,000 ml of warm water of 50° C. was added to the washed precipitate, and the resulting mixture was stirred for 20 minutes and then filtered. The residue was dried at 60° C. and pulverized to obtain 35.97 g of a brown powder. This powder was heated in air at 350° C. for 5 hours and then cooled to room temperature to obtain 33.83 g of a black powder. Subsequently, this powder was heated in a hydrogen stream at 180° C. for 5 hours to obtain copper-based catalyst G. As a result of analysis, the alkali metal content of the catalyst was found to be 0.02 wt% based on the catalyst's weight before the reduction with hydrogen.

Catalyst Preparation Example 8

Copper-based catalyst H was prepared according to the Catalyst Preparation Example 7 except for adding a solution of 0.0130 g of sodium carbonate in 40 ml of water to 5.0 g of the black powder obtained by the heating in air, and then evaporating the water with a rotary evaporator to support sodium carbonate on the powder by impregnation. As a result of analysis, the alkali metal content of the catalyst was found to be 0.14 wt% based on the catalyst's weight before the reduction with hydrogen.

Catalyst Preparation Example 9

Copper-based catalyst I was prepared according to the Catalyst Preparation Example 8 except for changing the amount of sodium carbonate to be supported by impregnation to 0.0265 g. As a result of analysis, the alkali metal content of the catalyst was found to be 0.24 wt% based on the catalyst's weight before the reduction with hydrogen.

Catalyst Preparation Example 10

Copper-based catalyst J was prepared according to the Catalyst Preparation Example 8 except for changing the amount of sodium carbonate to be supported by impregnation to 0.0510 g. As a result of analysis, the alkali metal content of the catalyst was found to be 0.45 wt% based on the catalyst's weight before the reduction with hydrogen.

Catalyst Preparation Example 11

Copper-based catalyst K was prepared according to the Catalyst Preparation Example 8 except for changing the amount of sodium carbonate to be supported by impregnation to 0.1031 g. As a result of analysis, the alkali metal content of the catalyst was found to be 0.96 wt% based on the catalyst's weight before the reduction with hydrogen.

Catalyst Preparation Example 12

Copper-based catalyst L was prepared according to the Catalyst Preparation Example 8 except for supporting 0.0128 g of potassium carbonate by impregnation in place of sodium carbonate. As a result of analysis, the total contents of the alkali metals in the catalyst was found to be 0.15 wt% based on the catalyst's weight before the reduction with hydrogen.

Catalyst Preparation Example 13

48.32 g of copper nitrate trihydrate and 0.89 g of barium nitrate were dissolved in 400 ml of water, and the resulting solution was heated to 50° C. Then, a solution of 36.65 g of sodium carbonate in 200 ml of water was added dropwise with stirring over a period of 1 hour, after which the stirring was continued at the same temperature for 2 hours. The precipitate thus formed was collected by filtration and then washed 8 times with 1,000 ml of warm water of 50° C. Subsequently, a suspension of 16.80 g of Aerosil Silica in 1,000 ml of warm water of 50° C. was added to the washed precipitate, and the resulting mixture was stirred for 20 minutes and then filtered. The residue was dried at 60° C. and pulverized to obtain 35.69 g of a brown powder. This powder was heated in air at 350° C. for 5 hours and then cooled to room temperature to obtain 32.10 g of a black powder. A solution consisting of 0.0249 g of sodium carbonate and 40 ml of water was added to 5.0 g of the black powder, after which the water was evaporated with a rotary evaporator to support sodium carbonate on the solid by impregnation. Subsequently, the thus treated solid was heated in a hydrogen stream at 180° C. for 5 hours to obtain copper-based catalyst M. As a result of analysis, the weight ratio of metallic copper to barium carbonate in the catalyst was found to be 99.7:0.3, and the alkali metal content of the catalyst was found to be 0.20 wt% based on the catalyst's weight before the reduction with hydrogen.

Catalyst Preparation Example 14

Copper-based catalyst N was prepared according to the Catalyst Preparation Example 13 except for using 1.58 g of calcium nitrate tetrahydrate in place of barium nitrate and changing the amount of sodium carbonate to be supported by impregnation to 0.0252 g. As a result of analysis, the weight ratio of metallic copper to calcium carbonate in the catalyst was found to be 99.2:0.8, and the alkali metal content of the catalyst was found to be 0.20 wt% based on the catalyst's weight before the reduction with hydrogen.

Catalyst Preparation Example 15

12.8 g of diatomaceous earth was suspended in 200 ml of water, followed by adding thereto a solution of 48.3 g of copper nitrate trihydrate in 200 ml of water, and the resulting mixture was heated to 50° C. Then, a solution of 22.8 g of sodium carbonate in 200 ml of water was added dropwise with stirring over a period of 2 hours, after which the stirring was continued at the same temperature for 1 hour. The precipitate thus formed was collected by filtration and washed 3 times with 500 ml of warm water of 45° C. A solution of 1.27 g of sodium carbonate in 200 ml of water was added to the washed precipitate, and the resulting mixture was stirred. Thereafter, the water was evaporated with a rotary evaporator and the residue was dried at 60° C. and pulverized to obtain a dark-gray powder. In air, 35.1 g of this powder was heated at 350° C. for 5 hours and then cooled to room temperature to obtain 29.9 g of a black powder. Subsequently, this powder was heated in a hydrogen stream at 190° C. for 1.5 hours and then at 195° C. for 1 hour to obtain copper-based catalyst O.

Catalyst Preparation Example 16

43.5 g of copper nitrate trihydrate and 5.1 g of magnesium nitrate hexahydrate were dissolved in 350 ml of water, followed by suspending therein 15.9 g of Aerosil Silica, and the resulting suspension was heated to 50° C. Then, a solution of 21.5 g of sodium carbonate in 200 ml of water was added dropwise with stirring over a period of 2 hours, after which the stirring was continued at the same temperature for 1 hour. The precipitate thus formed was collected by filtration and then washed 3 times with 500 ml of warm water of 50° C. The washed precipitate was dried at 60° C. and pulverized to obtain a light-blue powder. In air, 47.0 g of this solid was heated at 350° C. for 1 hour and then cooled to room temperature to obtain 40.0 g of a black powder. Subsequently, this powder was heated in a hydrogen stream at 200° C. for 3 hours to obtain copper-based catalyst P. The theoretical weight ratio of metallic copper to magnesium carbonate in the catalyst was 87.2:12.8.

Catalyst Preparation Example 17

10.9 g of copper nitrate trihydrate and 1.06 g of strontium nitrate were dissolved in 200 ml of water, and 4.1 g of Aerosil Silica was suspended therein at 25° C. Then, a solution of 5.6 g of sodium carbonate in 60 ml of water was added dropwise with stirring over a period of 1 hour, after which the stirring was continued at the same temperature for 1.5 hours. The precipitate thus formed was collected by filtration and then washed 4 times with 400 ml of warm water of 25° C. The washed precipitate was dried at 60° C. and pulverized to obtain a light-blue powder. This powder was heated in air at 350° C. for 5 hours and then cooled to room temperature to obtain a black powder. Subsequently, this powder was heated in a hydrogen stream at 200° C. for 3 hours to obtain copper-based catalyst Q. The theoretical weight ratio of metallic copper to strontium carbonate in the catalyst was 79.5:20.5.

Catalyst Preparation Example 18

48.32 g of copper nitrate trihydrate was dissolved in 400 ml of water, and the resulting solution was heated to 50° C. Then, 46.3 ml of a 25 wt% aqueous ammonia solution was added dropwise with stirring over a period of 45 minutes, after which the stirring was continued at the same temperature for 4 hours. 16.0 grams of Aerosil Silica was added and the resulting mixture was continuously stirred for 20 minutes. Thereafter, the aqueous ammonia solution was evaporated with a rotary evaporator. The residue was dried and then pulverized to obtain 65.52 g of a brown powder. This powder was heated in air at 350° C. for 5 hours and then cooled to room temperature to obtain 29.25 g of a black powder. Subsequently, this powder was heated in a hydrogen stream at 180° C. for 5 hours to obtain copper-based catalyst R containing neither an alkali metal nor an alkaline earth metal.

Catalyst Preparation Example 19

Copper-based catalyst S containing no alkaline earth metal was prepared according to the Catalyst Preparation Example 16 except for changing the amount of copper nitrate trihydrate to 48.2 g and omitting magnesium nitrate hexahydrate.

Catalyst Preparation Example 20

12.7 g of diatomaceous earth was suspended in 200 ml of water, followed by adding thereto a solution of 48.4 g of copper nitrate trihydrate in 200 ml of water, and the resulting mixture was stirred and then heated to 50° C. Thereafter, a solution of 13.6 g of ammonium carbonate in 200 ml of water was added dropwise with stirring over a period of 2 hours, after which the stirring was continued at the same temperature for 1 hour. The precipitate thus formed was dried at 60° C. with a rotary evaporator and pulverized to obtain a light-blue powder. In air, 61.7 g of this powder was heated at 350° C. for 1 hour and then cooled to room temperature to obtain 28.9 g of a black powder. Subsequently, this powder was heated in a hydrogen stream at 180° C. for 1 hour to obtain copper-based catalyst T containing neither an alkali metal nor an alkaline earth metal.

Catalyst Preparation Example 21

Copper-based catalyst U was prepared according to the Catalyst Preparation Example 8 except for supporting 0.0127 g of sodium nitrate by impregnation in place of sodium carbonate. As a result of analysis, the alkali metal content of the catalyst was found to be 0.09 wt% based on the catalyst's weight before the reduction with hydrogen.

Example 1

Under nitrogen, 0.3 g of copper-based catalyst A was charged in a 150-ml stainless-steel autoclave equipped with a magnetic stirrer, and the autoclave was closed. Then, 50.0 g of acetophenone was charged in the autoclave and hydrogen was supplied thereto at 10 kg/cm$^2$. The acetophenone contained 0.33% impurities. The autoclave was put in an oil bath and the reaction was carried out with heating and stirring at 1,150 r.p.m. The temperature of the oil bath was 180° C. (The reaction was terminated 46.8 minutes after the start of the hydrogen supply and the reaction mixture was cooled to room temperature.) After the termination of the reaction, the autoclave was opened, followed by sampling and analysis by gas chromatography. The reaction mixture contained 22.87 wt% of acetophenone, 75.36 wt % of α-phenylethyl alcohol and 1.15 wt% of ethylbenzene. The conversion of acetophenone was 77.05%, the selectivity for α-phenylethyl alcohol was 96.52%, and the selectivity for ethylbenzene was 1.70%. The acetophenone-hydrogenating activity per unit time of 1.0 g of the catalyst was 1.37 mol/g·hr.

Example 2

The process of Example 1 was repeated except for using copper-based catalyst B in place of copper-based catalyst A and terminating the reaction 55.8 minutes after the start of the hydrogen supply. The reaction mixture contained 23.10 wt% of acetophenone, 75.62 wt% of α-phenylethyl alcohol and 0.608 wt% of ethylbenzene. The conversion of acetophenone was 76.82%, the selectivity for α-phenylethyl alcohol was 97.14%, and the selectivity for ethylbenzene was 0.90%. The acetophenone-hydrogenating activity per unit time of 1.0 g of the catalyst was 1.14 mol/g·hr.

Example 3

The process of Example 1 was repeated except for using copper-based catalyst C in place of copper-based catalyst A and terminating the reaction 54.1 minutes after the start of the hydrogen supply. The reaction mixture contained 23.42 wt% of acetophenone, 74.71 wt% of α-phenylethyl alcohol and 1.18 wt% of ethylbenzene. The conversion of acetophenone was 76.50%, the selectivity for α-phenylethyl alcohol was 96.38%, and the selectivity for ethylbenzene was 1.75%. The acetophenone-hydrogenating activity per unit time of 1.0 g of the catalyst was 1.17 mol/g·hr.

Example 4

The process of Example 1 was repeated except for using copper-based catalyst D in place of copper-based catalyst A and terminating the reaction 62.0 minutes after the start of the hydrogen supply. The reaction mixture contained 23.33 wt% of acetophenone, 75.50 wt% of α-phenylethyl alcohol and 0.75 wt% of ethylbenzene. The conversion of acetophenone was 76.60%, the selectivity for α-phenylethyl alcohol was 97.28%, and the selectivity for ethylbenzene was 0.75%. The acetophenone-hydrogenating activity per unit time of 1.0 g of the catalyst was 1.05 mol/g·hr.

Example 5

The process of Example 1 was repeated except for using copper-based catalyst E in place of copper-based catalyst A and terminating the reaction 61.5 minutes after the start of the hydrogen supply. The reaction mixture contained 24.32 wt% of acetophenone, 73.94 wt% of α-phenylethyl alcohol and 1.06 wt% of ethylbenzene. The conversion of acetophenone was 75.60%, the selectivity for α-phenylethyl alcohol was 96.52%, and the selectivity for ethylbenzene was 1.59%. The acetophenone-hydrogenating activity per unit time of 1.0 g of the catalyst was 1.02 mol/g·hr.

Example 6

The process of Example 1 was repeated except for using copper-based catalyst F in place of copper-based catalyst A and terminating the reaction 72.0 minutes after the start of the hydrogen supply. The reaction mixture contained 23.08 wt% of acetophenone, 75.74 wt% of α-phenylethyl alcohol and 0.54 wt% of ethylbenzene. The conversion of acetophenone was 76.85%, the selectivity for α-phenylethyl alcohol was 97.27%, and the selectivity for ethylbenzene was 0.80%. The acetophenone-hydrogenating activity per unit time of 1.0 g of the catalyst was 0.87 mol/g·hr.

Example 7

The process of Example 1 was repeated except for using copper-based catalyst G in place of copper-based catalyst A and terminating the reaction 52.5 minutes after the start of the hydrogen supply. The reaction mixture contained 25.75 wt% of acetophenone, 72.46 wt% of α-phenylethyl alcohol and 1.10 wt% of ethylbenzene. The conversion of acetophenone was 74.17%, the selectivity for α-phenylethyl alcohol was 96.41%, and the selectivity for ethylbenzene was 1.68%. The acetophenone-hydrogenating activity per unit time of 1.0 g of the catalyst was 1.17 mol/g·hr.

Example 8

The process of Example 1 was repeated except for using copper-based catalyst H in place of copper-based catalyst A and terminating the reaction 58.9 minutes after the start of the hydrogen supply. The reaction mixture contained 23.04 wt% of acetophenone, 75.63 wt% of α-phenylethyl alcohol and 0.61 wt% of ethylbenzene. The conversion of acetophenone was 76.88%, the selectivity for α-phenylethyl alcohol was 97.08%, and the selectivity for ethylbenzene was 0.90%. The acetophenone-hydrogenating activity per unit time of 1.0 g of the catalyst was 1.08 mol/g·hr.

Example 9

The process of Example 1 was repeated except for using copper-based catalyst I in place of copper-based catalyst A and terminating the reaction 61.5 minutes after the start of the hydrogen supply. The reaction mixture contained 25.96 wt% of acetophenone, 72.90 wt% of α-phenylethyl alcohol and 0.49 wt% of ethylbenzene. The conversion of acetophenone was 73.96%, the selectivity for α-phenylethyl alcohol was 97.28%, and the selectivity for ethylbenzene was 0.74%. The acetophenone-hydrogenating activity per unit time of 1.0 g of the catalyst was 0.99 mol/g·hr.

Example 10

The process of Example 1 was repeated except for using copper-based catalyst J in place of copper-based catalyst A and terminating the reaction 80.5 minutes after the start of the hydrogen supply. The reaction mixture contained 20.20 wt% of acetophenone, 78.80 wt% of α-phenylethyl alcohol and 0.64 wt% of ethylbenzene. The conversion of acetophenone was 79.74%, the selectivity for α-phenylethyl alcohol was 97.53%, and the selectivity for ethylbenzene was 0.66%. The acetophenone-hydrogenating activity per unit time of 1.0 g of the catalyst was 0.82 mol/g·hr.

Example 11

The process of Example 1 was repeated except for using copper-based catalyst K in place of copper-based catalyst A and terminating the reaction 97.5 minutes after the start of the hydrogen supply. The reaction mixture contained 24.62 wt% of acetophenone, 74.53 wt% of α-phenylethyl alcohol and 0.25 wt% of ethylbenzene. The conversion of acetophenone was 75.30%, the selectivity for α-phenylethyl alcohol was 97.68%, and the selectivity for ethylbenzene was 0.37%. The acetophenone-hydrogenating activity per unit time of 1.0 g of the catalyst was 0.64 mol/g·hr.

Example 12

The process of Example 1 was repeated except for using copper-based catalyst L in place of copper-based catalyst A and terminating the reaction 54.1 minutes after the start of the hydrogen supply. The reaction mixture contained 23.26 wt% of acetophenone, 75.04 wt% of α-phenylethyl alcohol and 0.92 wt% of ethylbenzene. The conversion of acetophenone was 76.67%, the selectivity for α-phenylethyl alcohol was 96.60%, and the selectivity for ethylbenzene was 1.37%. The acetophenone-hydrogenating activity per unit time of 1.0 g of the catalyst was 1.18 mol/g·hr.

Example 13

The process of Example 1 was repeated except for using copper-based catalyst M in place of copper-based catalyst A and terminating the reaction 70.4 minutes after the start of the hydrogen supply. The reaction mixture contained 22.69 wt% of acetophenone, 76.14 wt% of α-phenylethyl alcohol and 0.57 wt% of ethylbenzene. The conversion of acetophenone was 77.24%, the selectivity for α-phenylethyl alcohol was 97.29%, and the selectivity for ethylbenzene was 0.84%. The acetophenone-hydrogenating activity per unit time of 1.0 g of the catalyst was 0.91 mol/g·hr.

Example 14

The process of Example 1 was repeated except for using copper-based catalyst N in place of copper-based catalyst A and terminating the reaction 60.3 minutes after the start of the hydrogen supply. The reaction mixture contained 23.73 wt% of acetophenone, 74.91 wt% of α-phenylethyl alcohol and 0.62 wt% of ethylbenzene. The conversion of acetophenone was 76.19%, the selectivity for α-phenylethyl alcohol was 97.03%, and the selectivity for ethylbenzen was 0.94%. The acetophenone-hydrogenating activity per unit time of 1.0 g of the catalyst was 1.05 mol/g·hr.

Example 15

Under nitrogen, 0.3 g of copper-based catalyst O was charged in a 50-ml stainless-steel autoclave equipped with a magnetic stirrer, and the autoclave was closed. Then, 15.0 g of acetophenone was charged in the autoclave and hydrogen was supplied thereto at 10 kg/cm². The acetophenone contained 1.59% impurities. The autoclave was put in an oil bath and the reaction was carried out with heating and stirring at 1,000 r.p.m. The temperature of the oil bath was 180° C. (The reaction was terminated 170 minutes after the start of the hydrogen supply and the reaction mixture was cooled to room temperature.) After the termination of the reaction, the autoclave was opened, followed by sampling and analysis by gas chromatography. The reaction mixture contained 9.99 wt% of acetophenone, 87.87 wt% of α-phenylethyl alcohol and 0.54 wt% of ethylbenzene. The conversion of acetophenone was 89.7%, the selectivity for α-phenylethyl alcohol was 99.3%, and the selectivity for ethylbenzene was 0.7%. The acetophenone-hydrogenating activity per unit time of 1.0 g of the catalyst was 0.23 mol/g·hr.

Example 16

Under nitrogen, 0.3 g of copper-based catalyst P was charged in a 50-ml stainless-steel autoclave equipped with a magnetic stirrer, and the autoclave was closed. Then, 15.0 g of acetophenone was charged in the autoclave and hydrogen was sealed up within the autoclave at 20 kg/cm². The acetophenone contained 0.33% impurities. The autoclave was put in an oil bath and the reaction was carried out with heating and stirring at 1,150 r.p.m. The temperature of the oil bath was 180° C. (The reaction was terminated 53 minutes after the start of the hydrogen supply and the reaction mixture was cooled to room temperature.) After the termination of the reaction, the pressure in the hydrogen gas holder was 8.0 kg/cm²G. The autoclave was opened, followed by sampling and analysis by gas chromatography. The reaction mixture contained 32.6 wt% of acetophenone, 66.8 wt% of α-phenylethyl alcohol and 0.6 wt% of ethylbenzene. The conversion of acetophenone was 67.1%, the selectivity for α-phenylethyl alcohol was 99.0%, and the selectivity for ethylbenzene was 1.0%. The acetophenone-hydrogenating activity per unit time of 1.0 g of the catalyst was 0.32 mol/g·hr.

Example 17

The process of Example 16 was repeated except for using copper-based catalyst Q in place of copper-based catalyst P and terminating the reaction 20 minutes after the start of the hydrogen supply. The reaction mixture contained 33.6 wt% of acetophenone, 65.2 wt% of α-phenylethyl alcohol and 1.2 wt% of ethylbenzene. The conversion of acetophenone was 66.4%, the selectivity for α-phenylethyl alcohol was 97.9%, and the selectivity for ethylbenzene was 2.1%.

Example 18

The process of Example 16 was repeated except for using copper-based catalyst S in place of copper-based catalyst P and terminating the reaction 24 minutes after the start of the hydrogen supply. The reaction mixture contained 31.3 wt% of acetophenone, 67.0 wt% of α-phenylethyl alcohol and 1.7 wt% of ethylbenzene. The conversion of acetophenone was 68.4%, the selectivity for α-phenylethyl alcohol was 97.2%, and the selectivity for ethylbenzene was 2.8%.

Example 19

The process of Example 1 was repeated except for using copper-based catalyst U in place of copper-based catalyst A and terminating the reaction 55.3 minutes after the start of the hydrogen supply. The reaction mixture contained 23.26 wt% of acetophenone, 75.19 wt% of α-phenylethyl alcohol and 0.90 wt% of ethylbenzene. The conversion of acetophenone was 76.67%, the selectivity for α-phenylethyl alcohol was 96.79%, and the selectivity for ethylbenzene was 1.33%. The acetophenone-hydrogenating activity per unit time of 1.0 g of the catalyst was 1.15 mol/g·hr.

Comparative Example 1

The process of Example 1 was repeated except that a product obtained by heating a commercially available copper-chromite catalyst (C-100, SAKAI CHEMICAL INDUSTRY Co., Ltd.) in a hydrogen stream at 180° C. for 5 hours was used in place of copper-based catalyst A, and that the reaction was terminated 72.2 minutes after the start of the hydrogen supply. The reaction mixture contained 26.61 wt% of acetophenone, 70.24 wt% of α-phenylethyl alcohol and 2.37 wt% of ethylbenzene. The conversion of acetophenone was 73.30%, the selectivity for α-phenylethyl alcohol was 94.56%, and the selectivity for ethylbenzene was 3.68%. The acetophenone-hydrogenating activity per unit time of 1.0 g of the catalyst obtained above was 0.84 mol/g·hr.

Comparative Example 2

The process of Example 1 was repeated except that copper-based catalyst R containing neither an alkali metal nor an alkaline earth metal was used in place of copper-based catalyst A, and the reaction was terminated 132.9 minutes after the start of the hydrogen supply. The reaction mixture contained 28.96 wt% of acetophenone, 66.97 wt% of α-phenylethyl alcohol and 3.35 wt% of ethylbenzene. The conversion of acetophenone was 70.94%, the selectivity for α-phenylethyl alcohol was 93.15%, and the selectivity for ethylbenzene was 5.36%. The acetophenone-hydrogenating activity per unit time of 1.0 g of the catalyst was 0.44 mol/g·hr.

Comparative Example 3

The process of Example 15 was repeated except for using copper-based catalyst T in place of copper-based catalyst O. The reaction mixture contained 72.11 wt% of acetophenone, 26.22 wt% of α-phenylethyl alcohol and 0.08 wt% of ethylbenzene. The conversion of acetophenone was 26.4%, the selectivity for α-phenylethyl alcohol was 99.6%, and the selectivity for ethylbenzene was 0.4%. The acetophenone-hydrogenating activity per unit time of 1.0 g of the catalyst was 0.07 mol/g·hr.

What is claimed is:

1. A process for producing α-phenylethyl alcohol by hydrogenation of acetophenone, which uses a copper-based catalyst containing at least one alkali metal compound.

2. A process for producing α-phenylethyl alcohol by hydrogenation of acetophenone, which comprises using a copper-based catalyst containing at least one alkaline earth metal carbonate.

3. A process for producing α-phenylethyl alcohol by hydrogenation of acetophenone, which comprises using a copper-based catalyst containing at least one alkaline earth metal carbonate and at least one alkali metal compound.

4. A process for producing α-phenylethyl alcohol by hydrogenation of acetophenone, which comprises using a copper-based catalyst containing at least one alkali metal compound and a silica carrier.

5. A process for producing α-phenylethyl alcohol by hydrogenation of acetophenone, which comprises using a copper-based catalyst containing at least one alkaline earth metal carbonate and a silica carrier.

6. A process for producing α-phenylethyl alcohol by hydrogenation of acetophenone, which comprises using a copper-based catalyst containing at least one alkaline earth metal carbonate, at least one alkali metal compound and a silica carrier.

7. The process according to claim 2, 3, 4, 5 or 6, wherein the alkaline earth metal carbonate is selected from the group consisting of calcium carbonate, strontium carbonate and barium carbonate.

8. The process according to claim 2, 3, 4, 5 or 6, wherein the alkaline earth metal carbonate is strontium carbonate.

9. The process according to claim 2, 3, 4 or 6, wherein the weight ratio of the alkaline earth metal carbonate(s) to metallic copper ranges from 0.1:99.9 to 50:50.

10. The process according to claim 2, 3, 4 or 6, wherein the weight ratio of the alkaline earth metal carbonate(s) to metallic copper ranges from 0.1:99.9 to 25:75.

11. The process according to claim 1, 3, 4 or 6, wherein the alkali metal compound is selected from the group consisting of sodium salts and potassium salts.

12. The process according to claim 1, 3, 4 or 6, wherein the alkali metal compound is selected from the group consisting of alkali metal carbonates and alkali metal nitrates.

13. The process according to claim 1, 3, 4 or 6, wherein the alkali metal compound is an alkali metal carbonate.

14. The process according to claim 1, 3, 4 or 6, wherein the alkali metal compound is selected from the group consisting of sodium carbonate, potassium carbonate and sodium nitrate.

15. The process according to claim 1, 3, 4 or 6, wherein the copper-based catalyst contains the alkali metal compound(s) in an amount of 0.01 to 10 wt% in terms of the alkali metal(s) before its reduction.

16. The process according to claim 1, 3, 4 or 6, wherein the copper-based catalyst contains the alkali metal compound(s) in an amount of 0.01 to 5 wt% in terms of the alkali metal(s) before its reduction.

17. The process according to claim 1, 2, 3, 4, 5 or 6, wherein the hydrogenation reaction temperature ranges from 50° to 200° C.

18. The process according to claim 1, 2, 3, 4, 5 or 6, wherein the hydrogenation reaction pressure ranges from 5 to 100 atmospheres.

19. The process according to claim 1, 2, 3, 4, 5 or 6, wherein the weight ratio of the catalyst used for the hydrogenation reaction to a material to be reduced ranges from 0.001:1 to 0.5:1.

20. The process according to claim 1, 2, 3, 4, 5 or 6, wherein in the hydrogenation reaction, the feed rate (LHSV) of a solution of a material to be reduced ranges from 0.1 to 5h$^{-1}$.

21. The process according to claim 1, 2, 3, 4, 5 or 6, wherein in the hydrogenation reaction, the amount of hydrogen used ranges from 1 to 30 times larger than the theoretical molar equivalent of hydrogen to a material to be reduced.

* * * * *